United States Patent [19]

Fischer et al.

[11] Patent Number: 5,580,994

[45] Date of Patent: Dec. 3, 1996

[54] PREPARATION OF TETRAHYDROPYRAN-4-CARBOXYLIC ACID AND ITS ESTERS

[75] Inventors: Rolf Fischer, Heidelberg; Werner Schnurr, Herxheim; Norbert Goetz, Worms; Thomas Kuekenhoehner, Boehl-Iggelheim, all of Germany

[73] Assignee: BASF Aktiengesellschaft, Ludwigshafen, Germany

[21] Appl. No.: 403,769

[22] PCT Filed: Dec. 23, 1993

[86] PCT No.: PCT/EP93/03670

§ 371 Date: Mar. 24, 1995

§ 102(e) Date: Mar. 24, 1995

[87] PCT Pub. No.: WO94/15931

PCT Pub. Date: Jul. 21, 1994

[30] Foreign Application Priority Data

Jan. 9, 1993 [DE] Germany .................. 43 00 419.9

[51] Int. Cl.$^6$ .............................................. C07D 309/06
[52] U.S. Cl. ................................................ 549/425
[58] Field of Search .............................................. 549/425

[56] References Cited

U.S. PATENT DOCUMENTS

| 4,837,346 | 6/1989 | Becker et al. ............. 549/425 |
| 5,371,246 | 12/1994 | Borchers et al. .......... 549/425 |
| 5,414,097 | 5/1995 | Fischer et al. ............ 549/425 |

FOREIGN PATENT DOCUMENTS 284969  10/1988  European Pat. Off.

OTHER PUBLICATIONS

J. Chem. Soc. 1930, pp. 2525 to 2530.

*Primary Examiner*—Nicky Chan
*Attorney, Agent, or Firm*—Keil & Weinkauf

[57] ABSTRACT

A process for preparing tetrahydropyran-4-carboxylic acid and its esters of the formula I

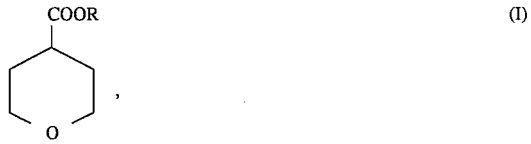

(R=H, $C_1$–$C_8$-alkyl, $C_3$–$C_8$-cycloalkyl, aryl, $C_7$–$C_{12}$-alkylphenyl and $C_7$–$C_{12}$-phenylalkyl) by reacting 2,7-dioxaspiro[4.4]nonane-1,6-dione II

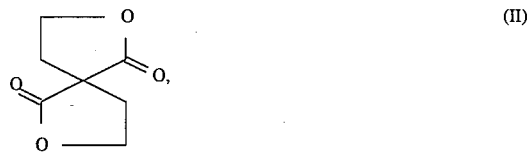

with water or alcohols III $$R\text{—OH} \qquad (III),$$

in the presence of acidic catalysts at from 150° to 350° C. and from 0.01 to 100 bar.

5 Claims, No Drawings

PREPARATION OF TETRAHYDROPYRAN-4-CARBOXYLIC ACID AND ITS ESTERS

This is an application under 35 USC § 371 of PCT/EP 93/03670 filed Dec. 23, 1993.

The present invention relates to a process for preparing tetra-hydropyran-4-carboxylic acid and its esters by reaction of 2,7-dioxaspiro[4.4]nonane-1,6-dione with water or alcohols in the presence of acidic catalysts at elevated temperatures.

From J. Chem. Soc. 1930, pages 2525 to 2530, a process for preparing tetrahydropyran-4-carboxylic acid esters is known in which β,β'-dichlorodiethyl ether is reacted with the sodium salt of diethyl malonate to give diethyl tetrahydropyran-4,4-dicarboxylate, and this is converted to tetrahydropyran-4-carboxylic acid via tetrahydropyran-4,4-dicarboxylic acid and finally esterified to give the desired tetrahydropyran-4-carboxylic acid ester.

EP-A-284 969 furthermore discloses preparing tetrahydropyran-4-carboxylic acid esters by reaction of 3-(2-hydroxyethyl)butyrolactone or its esters and ethers with alcohols in the presence of acidic catalysts.

A disadvantage of the known processes is that they proceed either in numerous reaction steps and with production of salt or only with low yields.

It is an object of the present invention to make the compounds I more accessible.

We have found that this object is achieved by a novel and improved process for preparing tetrahydropyran-4-carboxylic acid and its esters of the formula I

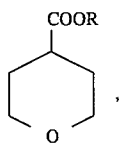

COOR   (I)

where R is hydrogen, $C_1$–$C_8$-alkyl, $C_3$–$C_8$-cycloalkyl, aryl, $C_7$–$C_{12}$-alkylphenyl or $C_7$–$C_{12}$-phenylalkyl, which comprises reacting 2,7-dioxaspiro[4.4]nonane-1,6-dione of the formula II

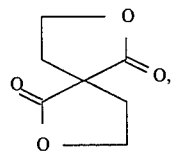

(II)

with water or alcohols of the formula III

R—OH   (III), in the presence of acidic catalysts at from 150° to 350° C. and from 0.01 to 100 bar.

The 2,7-dioxaspiro[4.4]nonane-1,6-dione II can preferably be reacted in molten (m.p.: 108° to 109° C.) or dissolved form, together with the alcohol III or water and, if appropriate, an inert gas such as nitrogen, carbon dioxide or argon, to give tetrahydropyran-4-carboxylic acid and its esters I.

Reaction temperatures of from 200° to 300° C., in particular from 220° to 270° C. and a pressure of from 0.1 to 5 bar are particularly advantageous.

The reaction can be performed batchwise or continuously, eg. as a solid-bed reaction using solid-bed catalysts, for example in a liquid-phase or trickle procedure in the liquid or gas phase, eg. in solid form in a fluidized bed or with solid-bed catalysts suspended in the liquid phase or homogeneous catalysts.

The material discharged from the reaction can be condensed by means of a suitable cooling device and then worked up by fractional distillation. The tetrahydropyran-4-carboxylic acid and its esters I can be separated off and unreacted 2,7-dioxaspiro-[4.4]nonane-1,6-dione II or the ethers or esters of 3-(2'-hydroxyethyl)dihydro-2(3H)furanone, eg. 3-(2'-methoxyethyl)dihydro-2-(3H)-furanone, which may be contained in the material discharged from the reaction, can be recycled (cf. EP-A-284 963).

The reaction in the liquid phase can be carried out, for example, in such a way that a mixture of 2,7-dioxaspiro [4.4]nonane-1,6-dione II and the respective alcohol III (or water) is heated to the desired reaction temperature in the presence of a suspended solid-bed catalyst or of a homogeneous dissolved catalyst. After the necessary reaction time has passed, the reaction mixture is cooled and the catalyst removed, eg. by filtration or neutralization. The reaction mixture can then be fractionally distilled to obtain the desired tetrahydropyran-4-carboxylic acid ester.

The molar ratio of alcohol III or water to the 2,7-dioxaspiro-[4.4]nonane-1,6-dione II is customarily from 0.5:1 to 50:1, preferably from 1:1 to 30:1, particularly preferably from 2:1 to 20:1.

In the case of heterogeneous catalysts, the reaction is carried out with catalyst loadings of from 0.1 to 10, in particular from 0.1 to 5, g of lactone II per g of catalyst and hour.

Suitable alcohols of the general formula III are, for example, methanol, ethanol, n-propanol, isopropanol, tert-butanol, n-butanol, isobutanol, sec-butanol, n-pentanol, n-hexanol, phenol, cyclopentanol and cyclohexanol. Methanol, ethanol, n-propanol and isopropanol are particularly suitable.

Suitable acidic catalysts are acidic homogeneous catalysts, in the liquid-phase reaction eg. mineral acids such as sulfuric acid, phosphoric acid, hydrochloric acid, nitric acid, hydrobromic acid or sulfonic acids such as benzenesulfonic acid and p-toluenesulfonic acid, but preferably heterogeneous catalysts, eg. acidic oxides of elements of main groups IIIA and IVA and of sub-groups IVB to VIB of the Periodic Table of the Elements. Examples of acidic heterogeneous catalysts which may be mentioned are silica in the form of silica gel, kieselguhr, quartz, titanium dioxide, zirconium dioxide, vanadium pentoxide, boron trioxide, aluminum oxide, chromium oxides, molybdenum oxides, tungsten oxides, zeolites such as the Y zeolites or mixtures thereof. Phosphorous pentoxide can also be employed as an acidic catalyst. Aluminum oxide is particularly preferred.

The molar ratio of acidic homogeneous catalyst to the 2,7-dioxaspiro[4.4]nonane-1,6-dione II is normally from 0,001:1 to 1:1, preferably from 0.01:1 to 0.1:1.

The 2,7-dioxaspiro[4.4]nonane-1,6-dione II can be prepared, for example, according to J. Chem. Soc., Perkin I (1977), pp. 521–530 by reaction of diethyl malonate with ethylene carbonate in the presence of sodium iodide, according to J. Org. Chem. Vol. 28 (1963), pp. 2809–2811 by hydrolysis of 1,5-dibromo-3,3-dicyanopentane with sulfuric acid or according to J. Org. Chem. Vol. 50 (1985), 1026–1031 by reaction of malonic acid with ethylene in the presence of manganese(III) acetate.

The substituent R in the compounds I and III has the following meanings:

R is $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, preferably $C_1$- to $C_4$-alkyl such as methyl, ethyl, n-propyl, isopropyl, n-butyl, isobutyl, sec-butyl and tertbutyl, particularly preferably methyl, ethyl, n-propyl and isopropyl, $C_3$–$C_8$-cycloalkyl such as cyclopropyl, cyclobutyl, cyclopentyl, cyclohexyl, cycloheptyl and cyclooctyl, preferably $C_5$- to $C_8$-cycloalkyl such as cyclopentyl, cyclohexyl, cycloheptyl and cyclooctyl, particularly preferably $C_5$- to $C_7$-cycloalkyl such as cyclopentyl, cyclohexyl and cycloheptyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$–$C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, preferably 2- and 4-methylphenyl, $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, preferably benzyl, 1-phenethyl and 2-phenethyl.

The tetrahydropyran-4-carboxylic acid esters obtainable by the process according to the invention are useful intermediates which can be processed, eg. to give tetrahydropyran-4-carbaldehyde (cf. DE-A-31 21 355, DE-A-33 14 816, DE-A-33 40 265, DE-A-38 21 197 and DE-A-40 39 918).

PREPARATION EXAMPLE 22 g per hour of a 20% strength solution of 2,7-dioxaspiro-[4.4]nonane-1,6-dione in methanol were added dropwise to a perpendicular tubular reactor via a heated dropping funnel (50° C.). 10 l/h of nitrogen were additionally metered in. In the upper part the reactor contained quartz rings and below 43 g of $Al_2O_3$ as a catalyst and was operated at 230° C. The gaseous material discharged from the reaction was condensed in cooling traps and analyzed by gas chromatography.

In this reaction 40 mol % of methyl tetrahydropyran-4-carboxylate, 33 mol % of 3-(2-methoxyethyl)dihydro-2(3H)furanone (recyclable by-product) and 14 mol % of 5-oxaspiro[2.4]heptan-4-one were formed. The methyl tetrahydropyran-4-carboxylate selectivity was therefore 60%.

We claim:

1. A process for preparing tetrahydropyran-4-carboxylic acid and its esters of the formula I

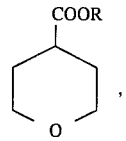

where R is hydrogen, $C_1$–$C_8$-alkyl, $C_3$–$C_8$-cycloalkyl, aryl, $C_7$–$C_{12}$-alkylphenyl or $C_7$–$C_{12}$-phenylalkyl, which comprises reacting 2,7-dioxaspiro[4.4]nonane-1,6-dione of the formula II

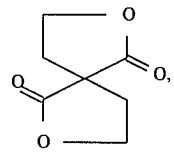

with water or alcohols of the formula III

in the presence of acidic catalysts at from 150° to 350° C. and from 0.01 to 100 bar.

2. A process for preparing tetrahydropyran-4-carboxylic acid and its esters of formula I as defined in claim 1, wherein the reaction is carried out at from 200° to 300° C.

3. A process for preparing tetrahydropyran-4-carboxylic acid and its esters of formula I as defined in claim 1, wherein the reaction is carried out at from 220° to 270° C.

4. A process for preparing tetrahydropyran-4-carboxylic acid and its esters of formula I as defined in claim 1, wherein the acidic catalysts used are acidic oxides of elements of main groups IIIA and IVA and of sub-groups IVB to VIB of the Periodic Table of the Elements.

5. A process for preparing tetrahydropyran-4-carboxylic acid and its esters of formula I as defined in claim 1, wherein the catalyst used is aluminum oxide.

* * * * *